United States Patent [19]

Takahashi et al.

[11] Patent Number: 5,347,994
[45] Date of Patent: Sep. 20, 1994

[54] ENDOSCOPE LIGHT SOURCE APPARATUS WITH SETTING ENABLE AND DISABLE MODES

[75] Inventors: Tadashi Takahashi; Katsuhiko Furuya, both of Tokyo, Japan

[73] Assignee: Asahi Kogaku Kogyo Kabushiki Kaisha, Tokyo, Japan

[21] Appl. No.: 903,576

[22] Filed: Jun. 24, 1992

[30] Foreign Application Priority Data

Jun. 27, 1991 [JP] Japan .................. 3-156527

[51] Int. Cl.$^5$ .................. A61B 1/04; G03B 29/00
[52] U.S. Cl. ........................ 128/6; 128/4; 354/62
[58] Field of Search ........ 354/62; 128/6, 4, 184, 128/731; 364/146, 188, 189, 160, 180; 200/43.01, 43.06, 43.09; 361/72; 362/85, 802

[56] References Cited

U.S. PATENT DOCUMENTS

| | | | |
|---|---|---|---|
| 3,518,383 | 6/1970 | Purpura | 200/43.09 |
| 4,404,496 | 9/1983 | Hosoda | 354/62 X |
| 4,409,987 | 10/1983 | McIntyre | 128/731 |
| 4,674,053 | 6/1987 | Bannai et al. | 364/146 |
| 4,723,207 | 2/1988 | Isobe et al. | 364/188 X |
| 4,773,008 | 9/1988 | Schroeder et al. | 364/146 X |
| 4,821,203 | 4/1989 | Carlton et al. | 364/188 X |
| 5,007,408 | 4/1991 | Ieoka | 128/6 |
| 5,115,261 | 5/1992 | Noda et al. | 354/62 |
| 5,159,380 | 10/1992 | Furuya et al. | 128/6 X |

FOREIGN PATENT DOCUMENTS 59-202427 11/1984 Japan .

Primary Examiner—Richard J. Apley
Assistant Examiner—John P. Leubecker
Attorney, Agent, or Firm—Sandler Greenblum & Bernstein

[57] ABSTRACT

A light source apparatus for an endoscope having a light source for supplying illuminating light to the endoscope. The light source apparatus includes a setting control device operable from the outside of the light source apparatus to make or change the setting of the light source apparatus. An operation mode changeover device is provided that is operable from the outside of the light source apparatus to change over a mode, wherein the setting can be made or changed by operating the setting control device, to a mode, wherein the setting cannot be made or changed, even if the setting control device is operated.

8 Claims, 9 Drawing Sheets

5,347,994

ENDOSCOPE LIGHT SOURCE APPARATUS WITH SETTING ENABLE AND DISABLE MODES

BACKGROUND OF THE INVENTION

The present disclosure relates to subject matter contained in Japanese Patent Application No. 3-156527 (filed on Jun. 27, 1991), which is expressly incorporated herein by reference in its entirety.

1. Field of the Invention

The present invention relates to a light source apparatus for an endoscope having an automatic exposure device for effecting photography by supplying illuminating light to the endoscope.

2. Description of the Prior Art

In general, a light source apparatus for an endoscope incorporates not only a light source lamp but also other devices, for example, a device for automatically controlling the brightness of lighting, an automatic exposure device for photography, etc. In addition, various switches for setting and changing the lighting brightness level, photographic conditions and so forth are provided on the panel of the light source apparatus such that these switches can be operated externally. By operating the switches, the photographic conditions and other conditions can be controlled as desired.

However, if it is possible to set and change photographic conditions and the like at any time by switch control, there is a possibility that someone may touch the switches by mistake or a undesirable third party may touch them intentionally during endoscopy, resulting in a change in the photographic conditions or the like. If the endoscopy continues under such conditions, serious problems will arise, for example, all the photographs taken will be of no use.

SUMMARY OF THE INVENTION

An object of the present invention is to provide a light source apparatus for an endoscope, which is designed so that it is possible for the user to set and change photographic conditions and other conditions for the light source apparatus as desired. Yet, it is impossible to readily set or change such conditions by mistake or by a third party.

Other objects and advantages of the present invention will become apparent from the following detailed description of an illustrated embodiment of the invention.

According to the present invention, there is provided a light source apparatus for an endoscope having a light source for supplying illuminating light to the endoscope. The light source includes a setting control device operatable from the outside of the light source apparatus to make or change the setting of the light source apparatus, and an operation mode changeover device operatable from the outside of the light source apparatus to change over a first mode wherein the setting can be made or changed by operating the setting control device, to and a second mode wherein the setting cannot be made or changed even if the setting control device is operated.

BRIEF DESCRIPTION OF THE DRAWINGS

The present invention may be more fully understood from the description of a preferred embodiment of the invention as set forth below, together with the accompanying drawings, in which.

DESCRIPTION OF THE EMBODIMENT

Figure 1:
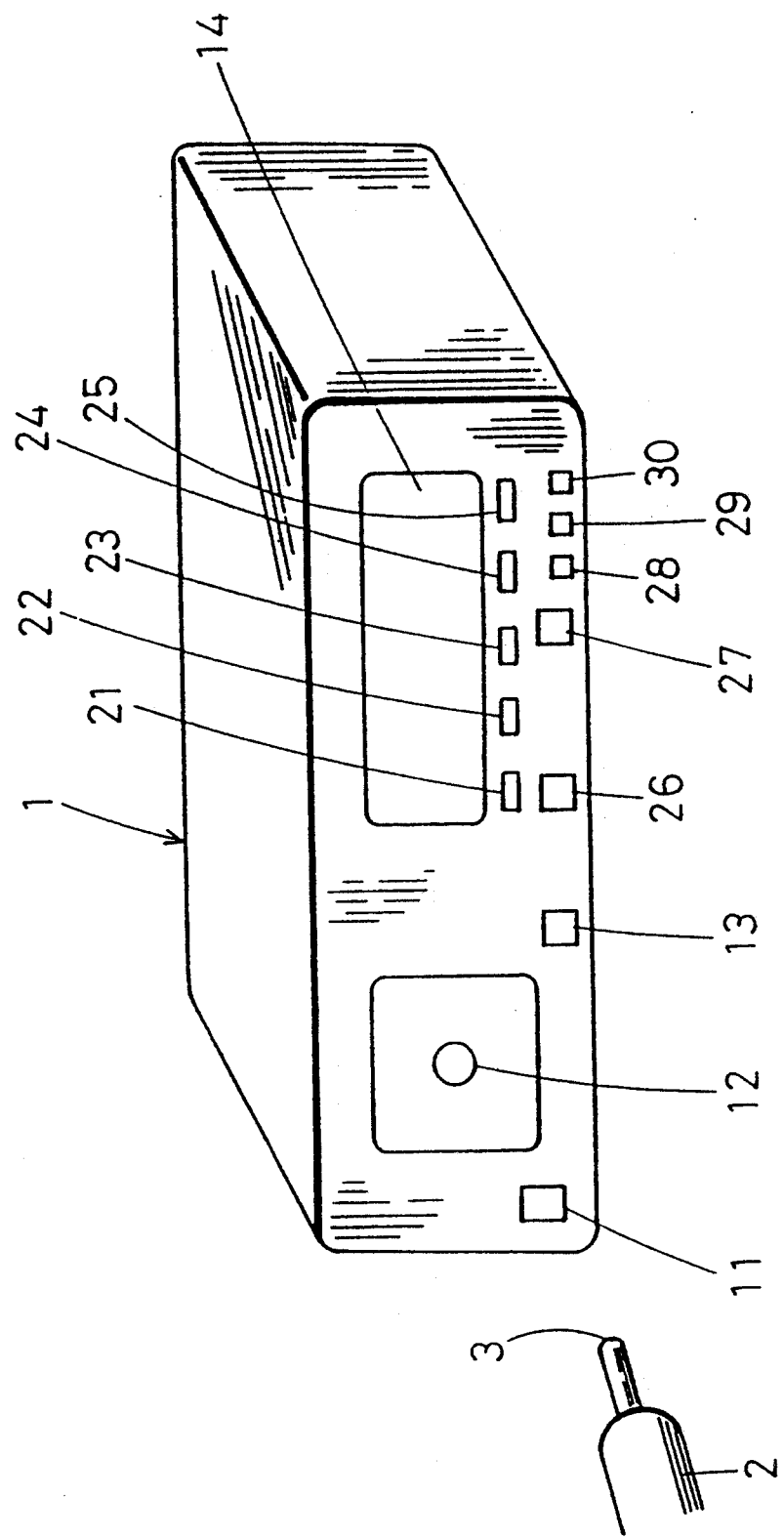
FIG. 1 shows the external appearance of one embodiment of the present invention.

FIG. 1 shows a light source apparatus 1 for an endoscope 2. Reference numeral 11 denotes a main power supply switch. A light guide socket 12, for insertion of an entrance end 3 of an illuminating light guide fiber bundle of the endoscope 2, is arranged such that light from a light source lamp 64 (shown in FIG. 2), incorporated in the light source apparatus 1, is condensed to the entrance end 3 of the illuminating light guide fiber bundle of the endoscope 2. A light source lamp switch 13 is used to turn ON/OFF the light source lamp 64.

A display 14, that comprises a liquid-crystal panel, for example, displays information including various conditions for effecting automatic exposure photography through the endoscope 2.

Pushbutton type function keys 21 to 25 are used with their functions changed according to circumstances. Functions of the keys 21 to 25, which are available at the present time, are displayed at the bottom line on the display 14.

It is possible with these function keys 21 to 25 to control the lighting brightness and the exposure index for automatic exposure photography and to set photographic conditions.

It should be noted that the above-described setting of photographic conditions includes the setting of a combination of the kind of endoscope used, the kind of photographic adapter attached to the endoscope, the sensitivity (speed) of a film used for photography, and the setting of an exposure index for the combination.

A pushbutton type lock switch 26 is used to select either a mode that enables control of the lighting brightness and the exposure index, or a mode that locks the lighting brightness and the exposure index in a set state to disable control of them. A light-emitting diode (LED) 26a, which will be explained in connection with FIG. 2, is associated with the lock switch 26 so as to actuate in response to the actuation of the lock switch 26.

An air pump switch 27 is used to turn ON/OFF an air pump 62 (shown in FIG. 2) that is incorporated in the light source apparatus 1, to send air to an air duct provided in the endoscope 2. When the switch 27 is engaged to actuate the pump 62, the "on" state is displayed "ON" the display 14.

Air pressure changeover switches 28 to 30 are used to change the air pressure from one level to another. The level of air pressure is displayed on the display 14. When two or all of the three air pressure changeover switches 28 to 30 are depressed simultaneously, the switch input, at this time, is invalid. It should be noted that when the input made through any of the switches 26 to 30 is valid, a short beep is sounded, whereas, when it is invalid, no beep is sounded.

Figure 2:
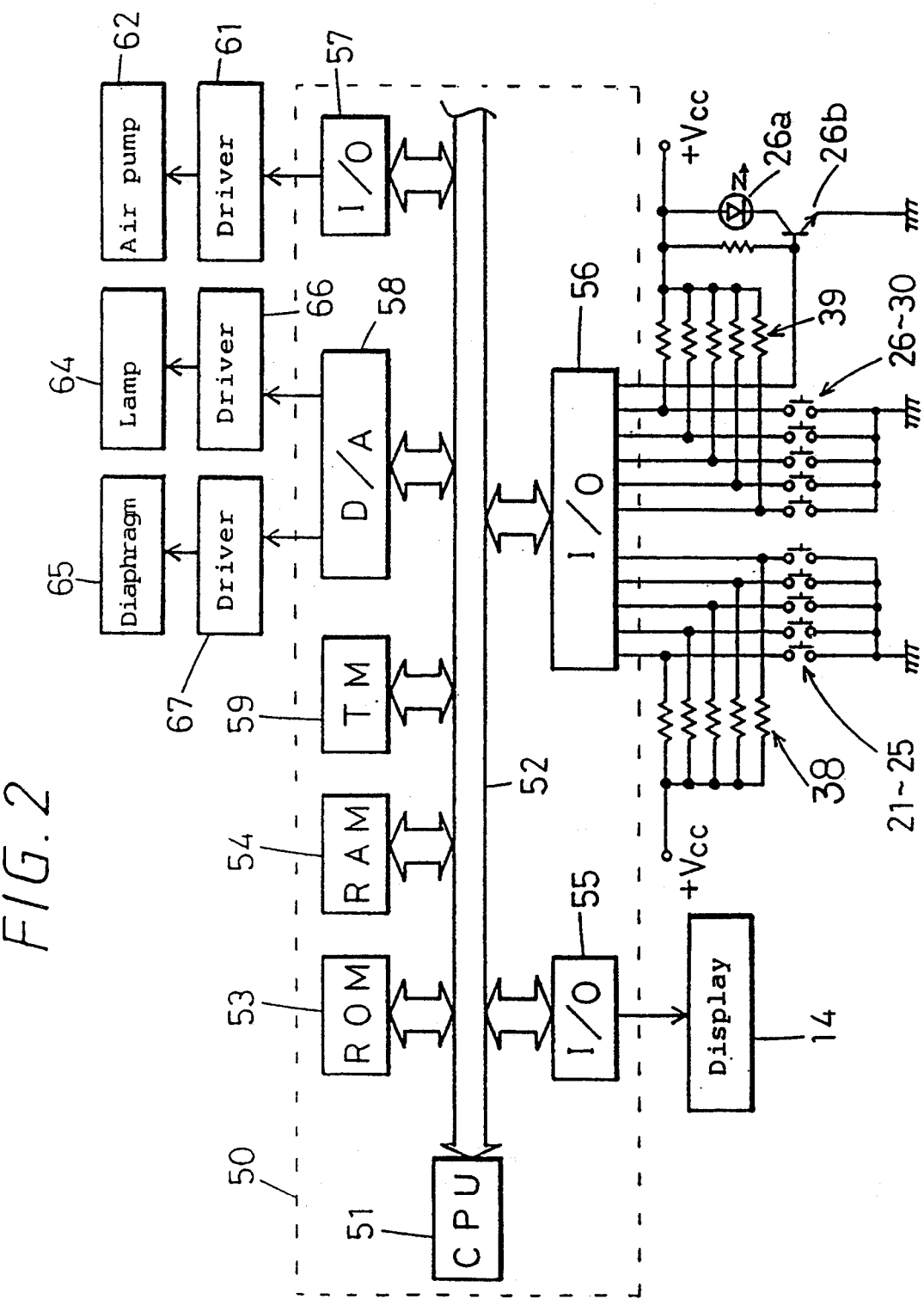
FIG. 2 is a circuit block diagram of the embodiment of the present invention.

FIG. 2 shows a control circuit that is provided in the light source apparatus 1. Reference numerals 21 to 30, in the figure, denote the above-described function and other keys.

A microcomputer 50 that executes control processing includes a central processing unit (CPU) 51, and a read-only memory (ROM) 53 stored with a software program, a random access memory (RAM) 54, a timer (TM) 59, input/output (I/O) ports 55 to 57 and a digital-to-analog (D/A) converter 58, which are connected to the CPU 51 through a system bus 52.

The first input/output port 55 is connected with the display 14. The second input/output port 56 is connected with the function and other switches 21 to 30. The third input/output port 57 is connected with the air pump 62 through a driver circuit 61.

The D/A converter 58 is connected with the light source lamp 64 through a driver circuit 66. The D/A converter 58 is also connected with a light quantity diaphragm 65 for varying the lighting brightness through a driver circuit 67, thereby allowing various control operations to be effected by the CPU 51, i.e., the control of the lighting brightness and also the control of the flash time of the light source lamp 64 for automatic exposure photography based on the set exposure index.

Pull-up resistors 38 and 39 are connected to respective lines. A light-emitting diode (LED) 26a turns on in response to the actuation of the lock switch 26 through a switching transistor 26b. Although the display 14 includes a driver circuit, a character generator, etc., illustration thereof is omitted.

Next, the operation of the apparatus of this embodiment will be explained with reference to FIGS. 3 to 9, which are flowcharts showing the software program stored in the ROM 53. In these figures, S denotes a processing step.

Figure 3:
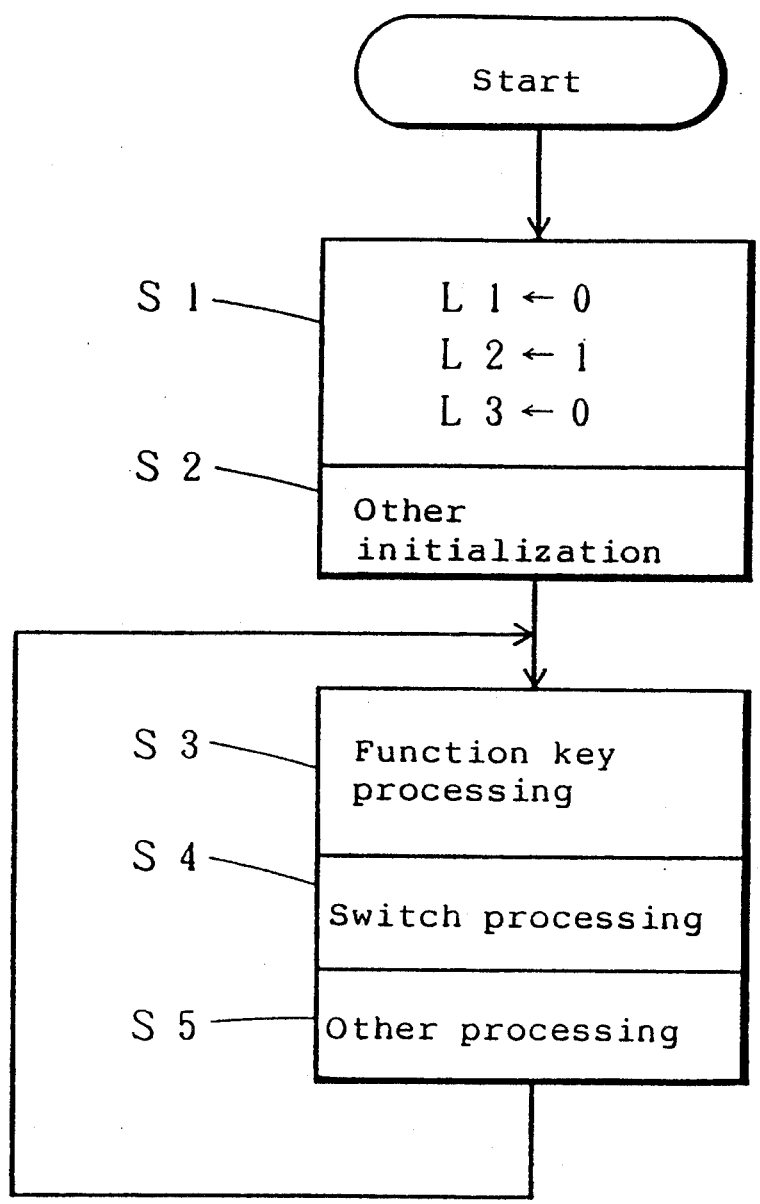
FIG. 3 is a flowchart of software in the embodiment of the present invention.

FIG. 3 shows the general flow of control process executed according to the software program. The process is started by turning on the main power supply switch 11 of the light source apparatus 1. First, initialization is executed to set variables L1, L2 and L3 to "0" "1" and "0" respectively, at S1. L1 shows a function key input state; L2 shows whether or not it is possible to set photographic conditions ("0" represents "possible"; "1" represents "impossible"). L3 shows whether or not it is possible to control the lighting brightness and the exposure index ("0" represents "possible"; "1" represents "impossible").

Accordingly, immediately after the power supply has been turned on, it is impossible to set photographic conditions, but it is possible to control the brightness and the exposure index.

After other initialization has been executed at 52, processing of the function keys 21 to 25 is executed at 53. In this embodiment, the function key processing is an operation of changing over the mode (L2=0) wherein it is possible to set photographic conditions, and the mode (L2=1) wherein it is impossible to do so when the fifth, third and first function keys 25, 23 and 21 are depressed sequentially within a predetermined time (e.g., 2 seconds).

After the function key processing at S3, switch processing is executed at S4. The switch processing is an operation of changing over the mode (L3=0) wherein it is possible to control the lighting brightness and the exposure index, and the mode (L3=1) wherein it is impossible to do so in response to the actuation of the lock switch 26.

After other processing has been executed at S5, the process returns to S3 to repeat the loop of S3 to S5. The time required for the process to round through the loop is sufficiently shorter than the length of time that an ON signal is being output when any of the switches 21 to 30 are depressed in an ordinary way.

Figure 4:
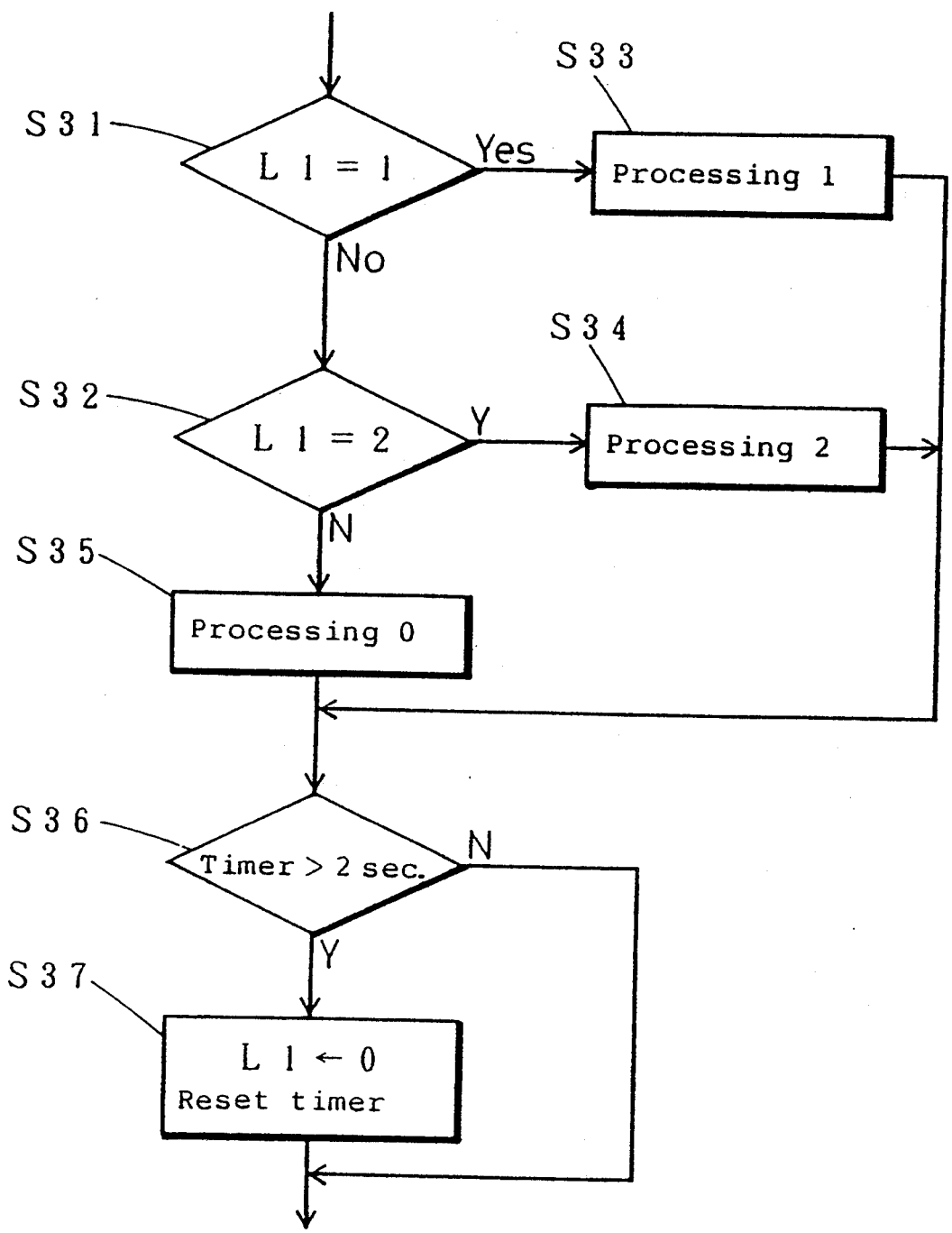
FIG. 4 is a flowchart of software in the embodiment of the present invention.

FIG. 4 shows the contents of the function key processing executed at S3. It is first judged at S31 whether L1 is "1" or not (i.e., "0" or "2"). If YES, processing "1" is executed at S33, whereas, if NO, it is then judged at S32 whether L1 is "2" or not (i.e., "0"). If YES is the answer at S32, processing "2" is executed at S34, whereas, if NO is the answer, processing "0" is executed at S35. After the processing "1", "2" or "0", it is judged at S36 whether the timer 59 exceeds 2 seconds. If YES, L1 is set to "0" and the timer 59 is reset at S37, and the process then proceeds to S4. If the timer 59 is not in excess of 2 seconds, the process proceeds directly to S4.

Figure 5:
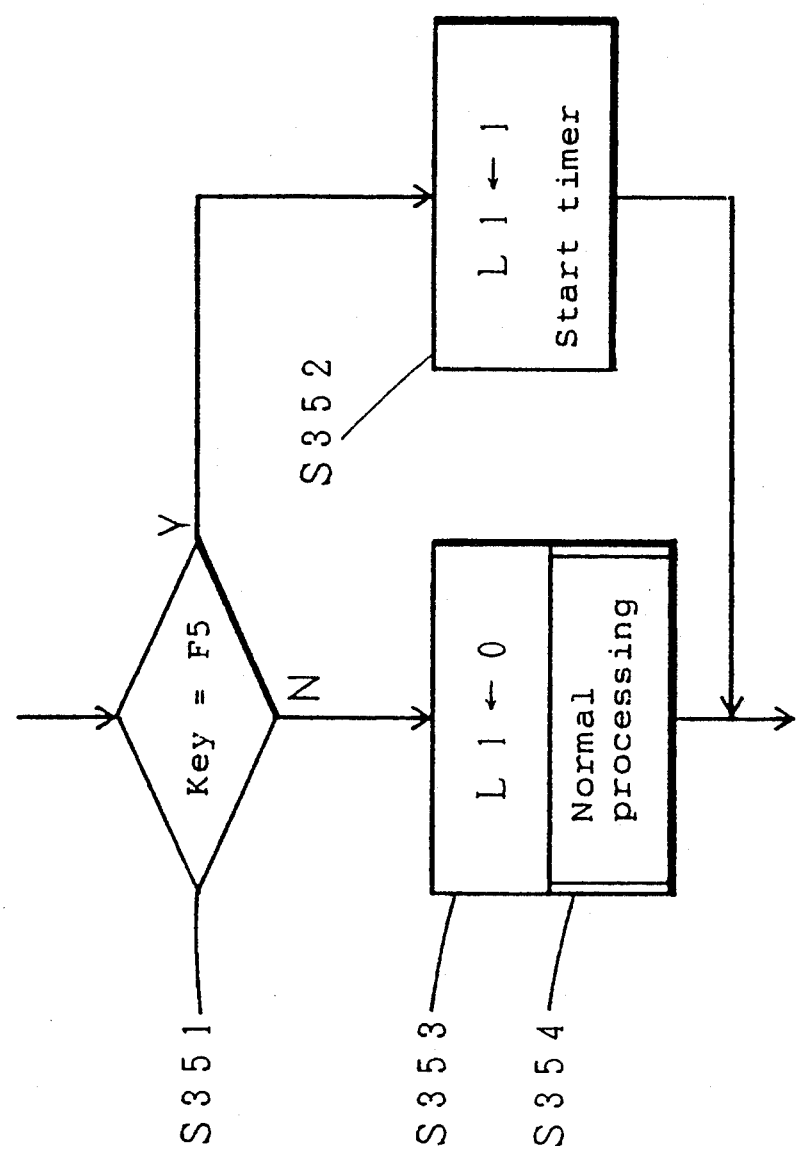
FIG. 5 is a flowchart of software in the embodiment of the present invention.

FIG. 5 shows the contents of the processing executed at 535 when L1 is decided to be "0" as a result of the judgement made at S31 and S32. If it is judged at S351 that the fifth function key 25 has been depressed, L1 is set to "1" and the timer 59 is started at S352, and the process then proceeds to S36. If the fifth function key 25 has not been depressed, L1 is set to "0" at S353, and normal processing is executed at S354. Then, the process proceeds to S36.

Figure 6:
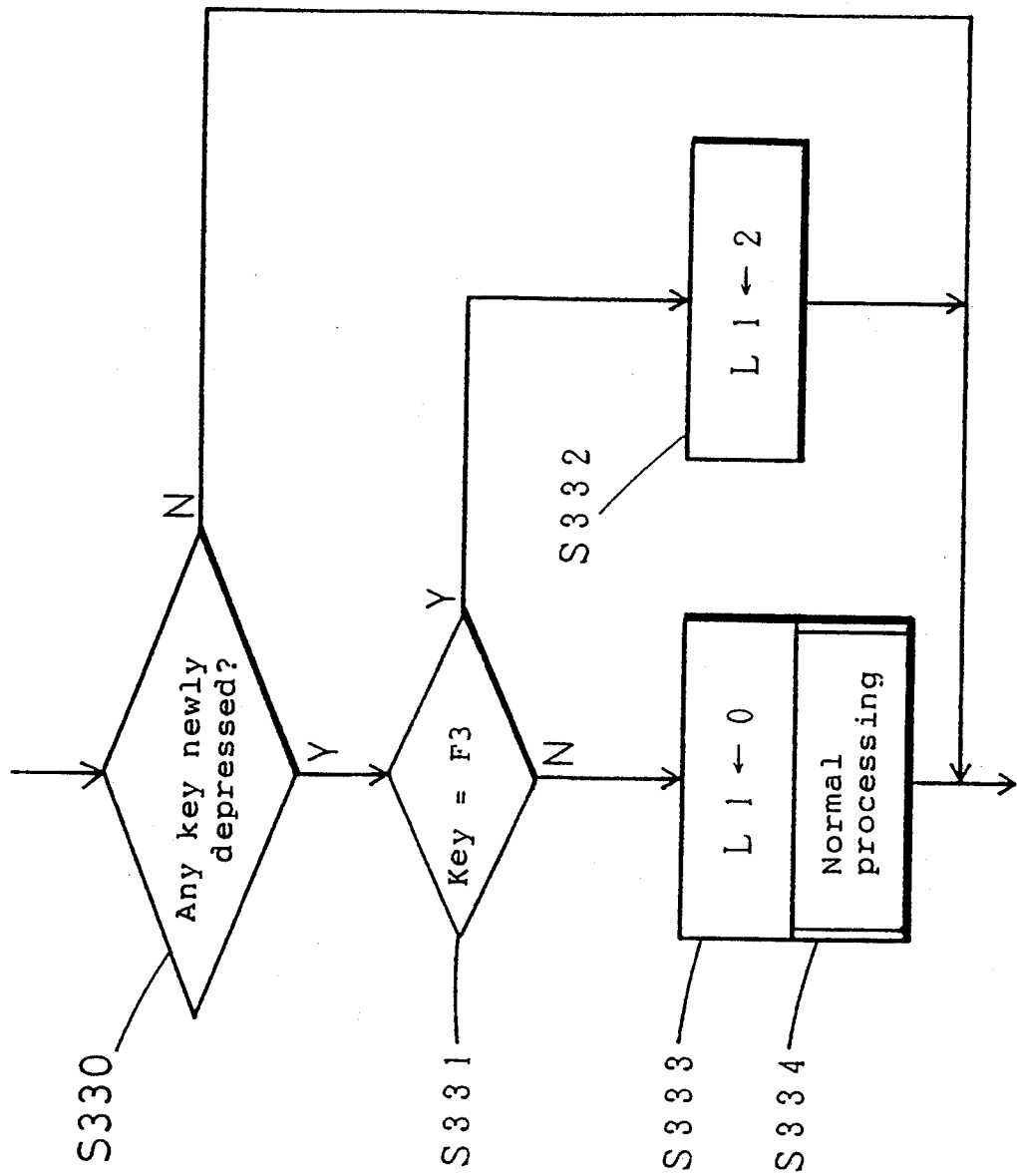
FIG. 6 is a flowchart of software in the embodiment of the present invention.

FIG. 6 shows the contents of the processing executed at S33 when L1 is judged to be "1" at S31, that is, when it is judged at S351 that the fifth function key 25 has already been depressed.

First, it is judged at S330 whether or not any switch has been newly depressed. The expression "newly depressed" is employed to exclude a case where it is judged at S330 that the fifth function key 25 has been continuously depressed after it has once been judged to be depressed at S351.

If it is judged at S330 that no key has been newly depressed, the process proceeds directly to S36, whereas, if it is judged that a key has been newly depressed, it is then judged at S331 whether or not the depressed key is the third function key 23.

If YES is the answer at S331, that is, if the third function key 23 has been depressed, L1 is set to "2" at S332, and the process then proceeds to S36. If the third function key 23 has not been depressed, L1 is set to "0" at S333, and normal processing is executed at S334, and then the process proceeds to S36.

Figure 7:
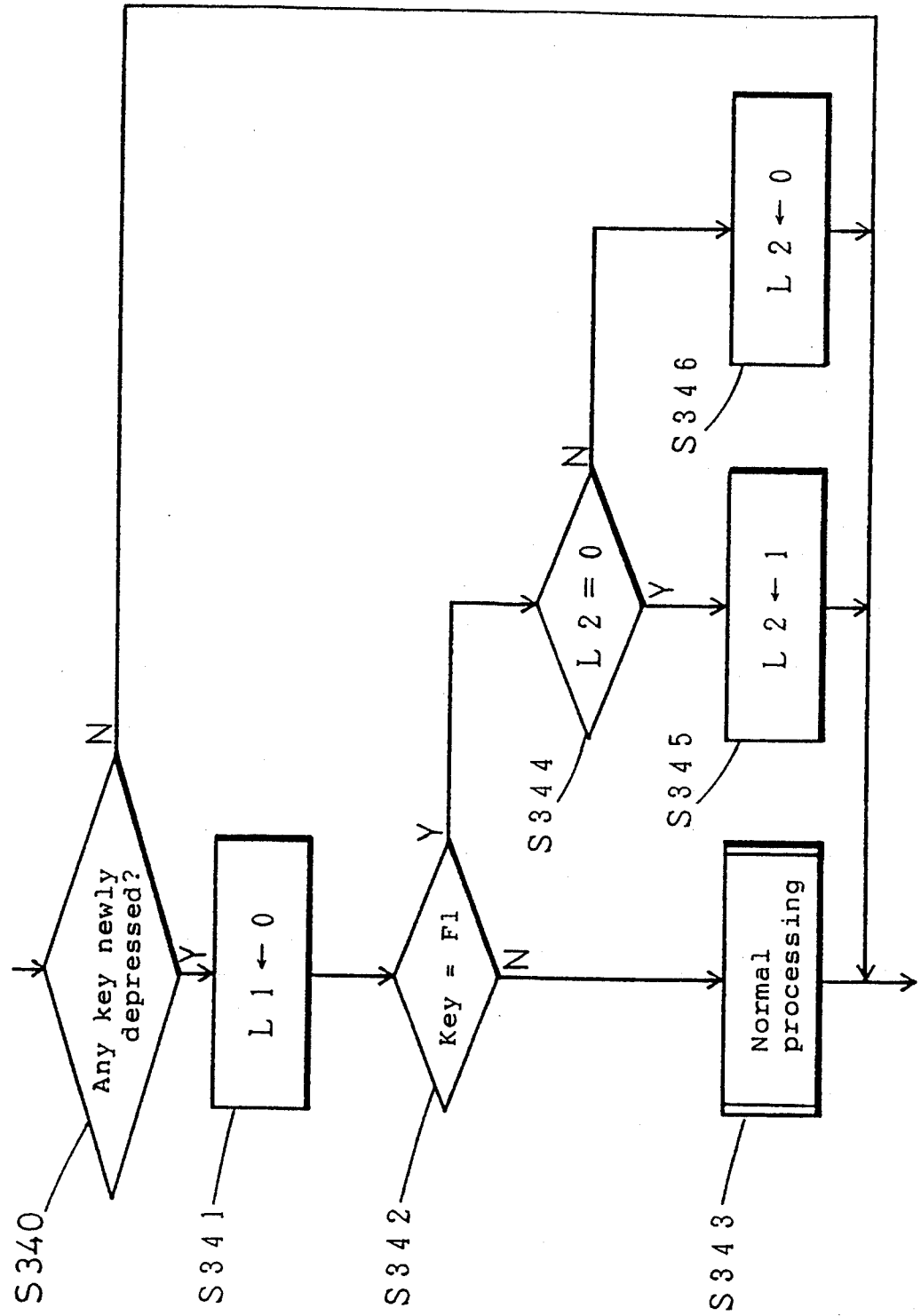
FIG. 7 is a flowchart of software in the embodiment of the present invention.

FIG. 7 shows the contents of the processing executed at S34 when L1 is judged to be "2" at S32, that is, when it is judged at S331 that the third function key 23 has already been depressed after the fifth function key 25.

First, it is judged at S340 whether or not any switch has been newly depressed in the same way as in the case of S330. If it is judged at S340 that no key has been newly depressed, the process proceeds directly to S36, whereas, if it is judged that a key has been newly depressed, L1 is set to "0" at S341, and it is then judged at S342 whether or not the depressed key is the first function key 21.

If the first function key 21 has not been depressed, normal processing is executed at S343, and then the process proceeds to S36. If the first function key 21 has been depressed, it is then judged at S344 whether or not L2 is "0". If L2 is "0", L2 is set to "1" at S345, and then the process proceeds to S36, whereas, if L2 is not "0", L2 is set to "0" at S346, and then the process proceeds to S36.

Figure 8:
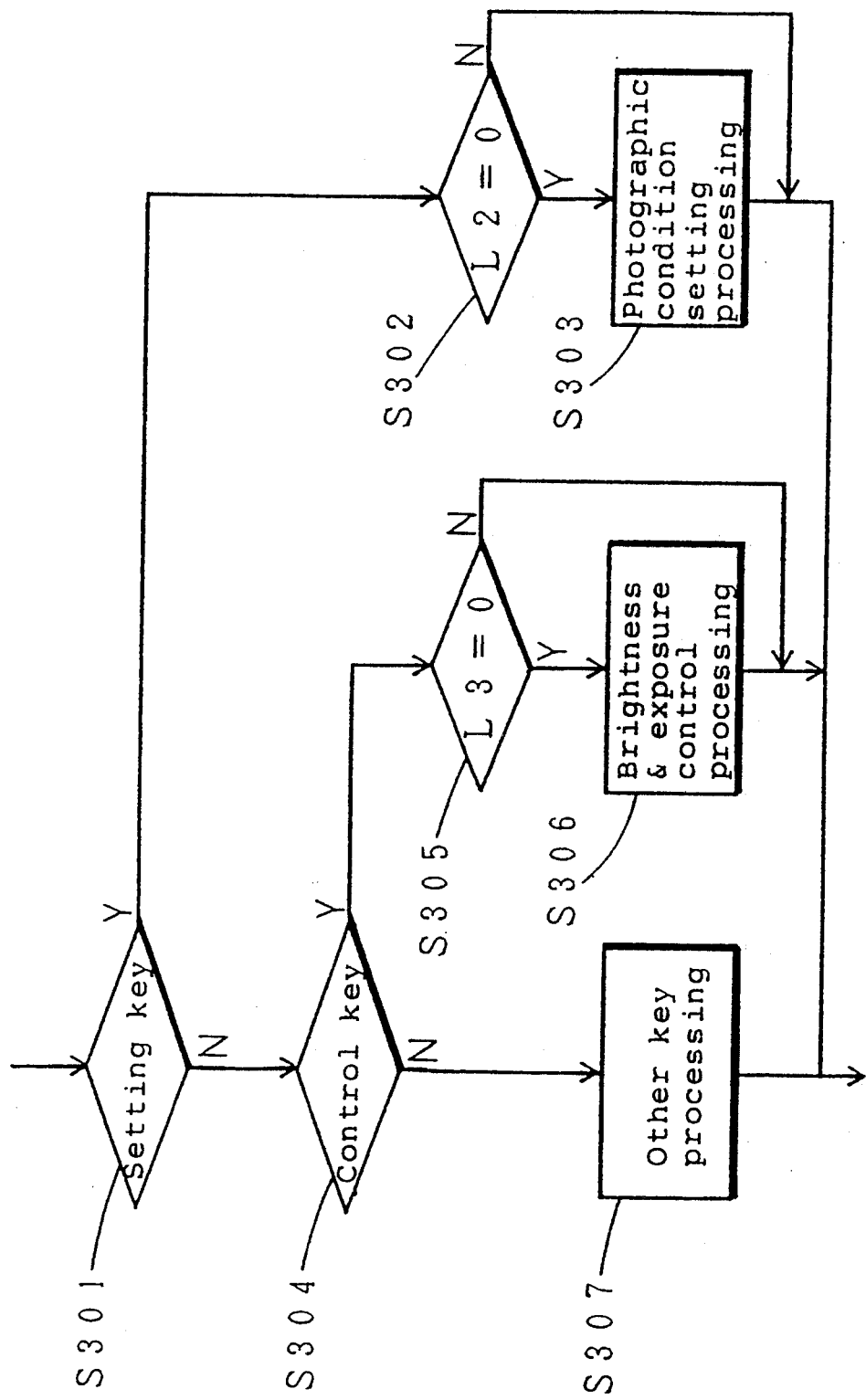
FIG. 8 is a flowchart of software in the embodiment of the present invention.

FIG. 8 shows the contents of the normal processing executed at S354, S334 and S343. First, it is judged at S301 whether or not a key of the function keys 21 to 25, concerned with the setting of photographic conditions (hereinafter referred to as "setting key"), has been depressed. If YES, it is then judged at S302 whether or not L2 is "0". If L2 is not "0", the process proceeds directly to S36, whereas, if L2 is "0", photographic condition setting processing is executed at S303 according to the function of the depressed key, and then the process proceeds to S36.

If it is judged at S301 that any setting key has not been depressed, it is then judged at S304 whether or not a key of the function keys 21 to 25 concerned with the control of the brightness and the exposure index (hereinafter referred to as "control key"), has been depressed. If the control key has been depressed, it is then judged at 5305 whether or not L3 is "0". If L3 is not "0", the process proceeds directly to S36 from S305, whereas, if L3 is "0", the brightness and exposure control processing is executed at S306 according to the function of the depressed key, and then the process proceeds to S36. If it is judged at S304 that any control key has not been depressed, either, the process proceeds to S307 to execute predetermined processing which is executed when another key is depressed. Then, the process proceeds to S36.

Figure 9:
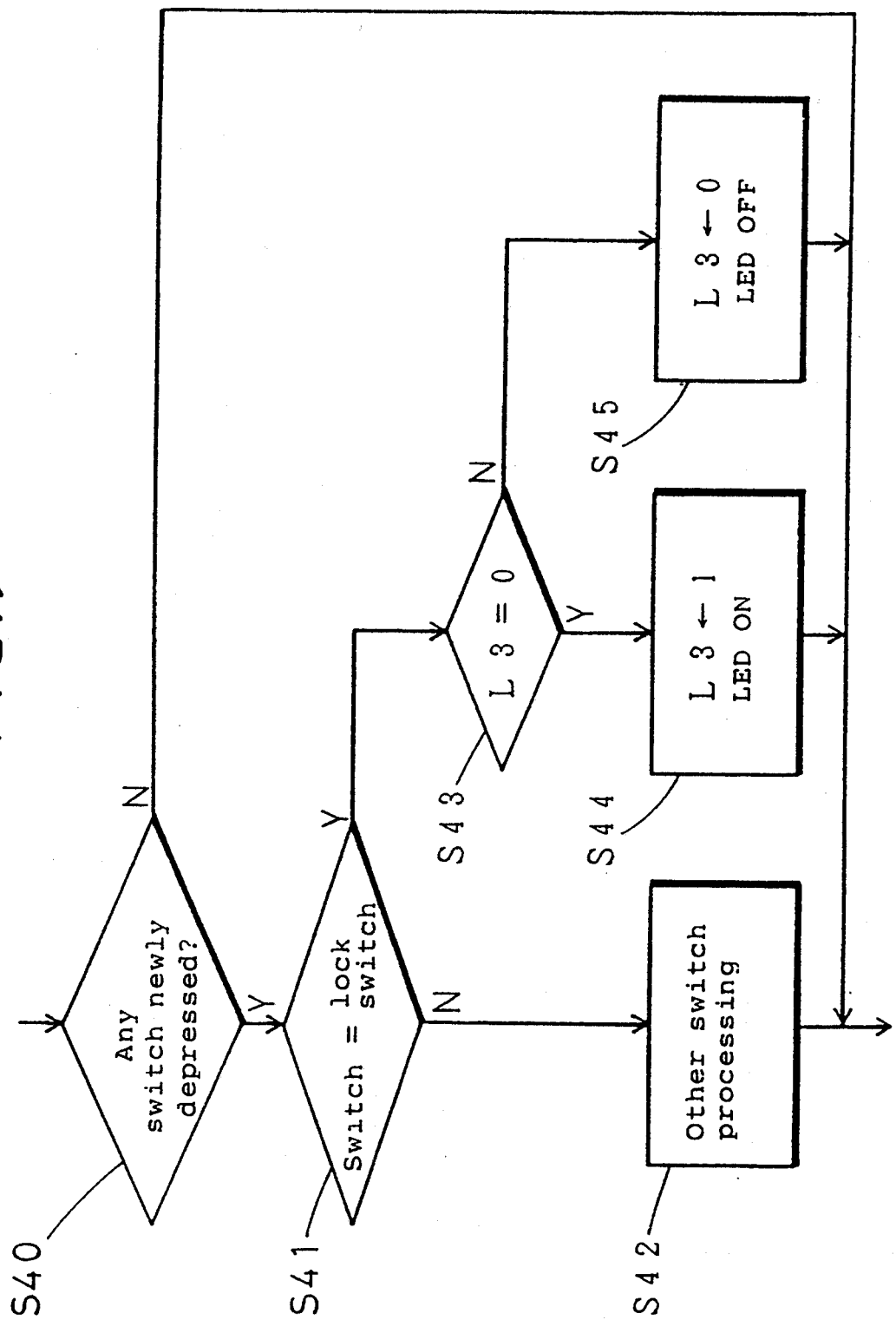
FIG. 9 is a flowchart of software in the embodiment of the present invention.

FIG. 9 shows the contents of the switch processing executed at S4. First, it is judged at S40 whether or not any switch has been newly depressed. If NO, the process proceeds directly to S5.

If it is judged at S40 that a switch has been depressed, it is then judged at S41 whether or not the depressed switch is the lock switch 26. If YES, it is then judged at S43 whether or not L3 is "0". If L3 is "0", L3 is set to "1" and the LED 26a is turned on at S44, and then the process proceeds to S5. If L3 is not "0", L3 is set to "0" and the LED 26a is turned off at S45, and then the process proceeds to S5.

If it is judged at S41 that the depressed switch is not the lock switch 26, predetermined processing for another switch is executed at S42, and then the process proceeds to S5. After other processing has been executed at S5, the process returns to S3 to repeat the loop of S3 to S5.

In the above-described processing, if the fifth function key 25 is depressed (S351), L1 is set to "1", whereas, if another key is depressed (S351), L1 remains at "0". If the third function key 23 is depressed (S331) within 2 seconds after the fifth function key 25 has been depressed, that is, when L1="1", L1 is set to "2" whereas if another key is depressed (S331), L1 is set to "0".

Further, if the first function key 21 is depressed (S342), within 2 seconds after the fifth function key 25 has been depressed, that is, when L1="2", the value of the variable L2 changes from "0" to "1" , or from "1" to "0", so that the photographic condition setting enable mode is changed over to the photographic condition setting disable mode, or the latter is changed over to the former.

Thus, in this embodiment, the photographic condition setting enable and disable modes are changed over from one to the other by depressing the fifth, third and first function keys 25, 23 and 21, sequentially within 2 seconds.

The central processing unit (51) operating under the software program stored in the ROM (53) provides the means for determining when these three function keys are depressed in the specific combination and within the given time. Accordingly, it is possible to set the system in the photographic condition setting disable mode, in which a third party cannot change the set mode easily and there is no possibility that the doctor (user) may change the set mode by mistake.

The above-described setting of photographic conditions includes the setting of a combination of the kind of endoscope used, the kind of photographic adapter attached to the endoscope, the sensitivity (speed) of a film used for photography, setting of an exposure index for the combination, and so on. The setting of such conditions is enabled only when L2="0", and when the process is at S303.

Accordingly, the setting of photographic conditions cannot be performed immediately after the main power supply switch 11 has been turned on. The photographic condition setting enable mode is established only when the above-described switch operation is executed, and it is returned to the photographic condition setting disable mode by executing a similar switch operation.

The control of the brightness of the light source lamp 64 and the exposure index is enabled only when L3="0" and when the process is at S306. Accordingly, the brightness of the light source lamp 64 and the exposure index can be changed (L3="0") immediately after the main power supply switch 11 has been turned on. When the lock switch 26 is depressed, it becomes impossible to change the brightness and the exposure index (L3="1"). When the lock switch 26 is depressed once more, it becomes possible to change them (L3="0"). Thereafter, each time the lock switch 26 is depressed, the brightness and exposure index enable and disable modes are changed over from one to the other. Accordingly, it is possible to set the system in the brightness and exposure index control disable mode by actuating the lock switch 26. This mode can be changed over to the control enable mode easily in comparison with the changeover of the photographic condition setting enable and disable modes.

It should be noted that the present invention is not necessarily limited to the above-described embodiment. For example, the system may be arranged such that the user can change the combination and the input sequence of the switch for changing over the photographic condition setting enable and disable modes as desired. The system may also be arranged such that the photographic condition setting enable and disable modes can be changed over with a single switch. In such a case, it is preferable to provide the switch at an inconspicuous position, e.g., on the side of the light source apparatus, so that it cannot readily be touched by a third party or by the user by mistake. Further, the processing at S303 and the processing at S306 in the above-described embodiment may be replaced with each other. That is, the arrangement may be such that the mode, wherein it is possible to control the brightness of the light source lamp 64 and the exposure index, and the mode, wherein it is impossible to do so, are changed over from one to the other by depressing specific switches.

According to the present invention, the operation control of the light source apparatus can be disabled by the operation mode changeover device, and it is therefore possible to prevent the set conditions of the light source apparatus from being changed undesirably by a third party. It is also possible to prevent an erroneous operation of a switch which would otherwise occur when the user touches it by mistake.

While the invention has been described by reference to a specific embodiment chosen for purposes of illustration, it should be apparent that numerous modifications could be made thereto by those skilled in the art without departing from the basic concept and scope of the invention.

We claim:

1. A light source apparatus for an endoscope having a light source for supplying illuminating light to said endoscope, said light source apparatus comprising:
   setting control means operable from the outside of said light source apparatus for making or changing a setting of said light source apparatus;
   operation mode changeover means operable from outside of said light source apparatus for switching from a first mode, wherein said first mode allows said setting control means to operate, to a second mode, wherein said second mode prevents said setting control means from operating; and
   said operation changeover means including a plurality of switches provided on said light source apparatus, and further including means for determining when said switches are operated in a specific combination such that said first and second modes are changed over from one to another.

2. A light source apparatus according to claim 1, wherein said plurality of switches are of a pushbutton type, and wherein said specific combination is a specific sequence within a specific time.

3. A light source apparatus according to claim 1, wherein said setting control means further comprises means for effecting automatic exposure photography through the endoscope.

4. A light source apparatus according to claim 3, wherein said setting includes a setting of a condition concerned with the automatic exposure photography.

5. A light source apparatus according to claim 4, wherein the setting includes a setting of a kind of endoscope used, a kind of photographic adapter attached to said endoscope and a sensitivity of a film used for photography.

6. A light source apparatus according to claim 4, wherein said setting includes a setting of a combination of a kind of endoscope used, a kind of photographic adapter attached to the endoscope, a sensitivity of a film used for photography, and a setting of an exposure index for said combination.

7. A light source apparatus according to claim 1, wherein said setting includes a setting of a brightness of illuminating light supplied from said light source to the endoscope.

8. A light source apparatus according to claim 4, wherein said setting includes a setting of an exposure index used to effect automatic exposure photography through the endoscope.

* * * * *